United States Patent [19]
Lehr

[11] Patent Number: 5,624,388
[45] Date of Patent: Apr. 29, 1997

[54] THERAPEUTIC ELBOW SUPPORT METHOD

[76] Inventor: Jay H. Lehr, 2268 Worthingwoods Blvd., Powell, Ohio 43065

[21] Appl. No.: 399,506

[22] Filed: Mar. 7, 1995

[51] Int. Cl.$^6$ .................................................. A61F 5/00
[52] U.S. Cl. .................................................. 602/20
[58] Field of Search .......................... 602/20, 26, 27, 602/62, 75, 23, 66; 428/121–130

[56] References Cited

U.S. PATENT DOCUMENTS

| | | | |
|---|---|---|---|
| 1,211,055 | 1/1917 | Bernstein | 602/66 X |
| 2,013,757 | 9/1935 | Jung, Jr. | 602/66 X |
| 3,785,371 | 1/1974 | Lewis . | |
| 3,789,842 | 2/1974 | Froimson | 602/62 X |
| 3,877,426 | 4/1975 | Nirschl | 602/62 X |
| 3,945,046 | 3/1976 | Stromgren . | |
| 4,198,708 | 4/1980 | Fugere et al. . | |
| 4,240,414 | 12/1980 | Theisler . | |
| 4,369,775 | 1/1983 | Gamm . | |
| 4,370,978 | 2/1983 | Palmubo . | |
| 4,377,160 | 3/1983 | Romaine | 602/75 X |
| 4,632,106 | 12/1986 | Gamm . | |
| 4,693,241 | 9/1987 | Trznadel . | |
| 4,805,606 | 2/1989 | McDavid, III . | |
| 4,807,607 | 2/1989 | Röder . | |
| 5,139,476 | 8/1992 | Peters . | |
| 5,338,290 | 8/1994 | Abound | 602/75 |
| 5,417,647 | 5/1995 | Down | 602/26 |

FOREIGN PATENT DOCUMENTS 2553996  5/1985  France .

OTHER PUBLICATIONS

Exhibit A, Donjoy Products Catalog, Rev A, pp. 62–63.

Primary Examiner—Richard J. Apley
Assistant Examiner—Kim M. Lee
Attorney, Agent, or Firm—Dinsmore & Shohl

[57] ABSTRACT

A therapeutic device for treating tendinitis and epicondylitis of the elbow is provided. The device comprises a loop of elastic material, wherein the loop has a 360-degree twist built therein so as to provide distinct first and second surfaces on the loop. The device is employed by positioning the loop about the elbow joint in a figure-8 formation, such that the loop is divided into an upper-band and a lower-band. The upper-band encircles the arm above and adjacent the elbow joint, the lower-band encircles the arm below and adjacent the elbow joint. The user then permits the loop to remain positioned about the elbow joint for a period sufficient to provide the desired relief.

14 Claims, 2 Drawing Sheets

THERAPEUTIC ELBOW SUPPORT METHOD

BACKGROUND OF THE INVENTION

1. Field of the Invention

The present invention pertains to a therapeutic device for the elbow joint, as well as a therapeutic method utilizing this device. More specifically, this device alleviates the discomfort associated with tendinitis and epicondylitis of the elbow by providing gentle pressure around the circumference of the elbow both above and below the joint.

2. Description of the Prior Art

Athletes participating in a variety of sports including tennis, other racket sports, baseball, golf and weight lifting, to name but a few, often experience discomfort in and around the elbow joint. Many of these ailments can be directly attributed to frequent rotation of the elbow, particularly when the arm is fully extended. Thus, while participants in racket sports are especially prone to such problems, even the continued use of hand-tools may cause similar discomfort.

Often the discomfort experienced is attributed to "tennis elbow," a term which is loosely employed to describe a number of different elbow complaints. Primarily, however, the term is used to describe lateral or medial epicondylitis or tendinitis of the associated tendons in the region. In the elbow joint, the flexor muscle of the forearm connects to the medial epicondyle (inside elbow protrusion of the humerus), and the extensor muscle connects to the lateral epicondyle (outside elbow protrusion of the humerus). These muscles are connected by tendons to the respective epicondyles of the humerus. Excessive tension in the flexor and extensor muscles (such as that caused by the activities describes previously) puts tremendous stress on the connection between the tendons and the epicondyles. The result can be inflammation of the epicondyles, also known as epicondylitis. Alternatively, or simultaneously, the tendons themselves may become inflamed, particularly if the tendon begins to pull away from the bone. This inflammation of the tendons is termed tendinitis.

As is often the case with overuse or repetitive-stress injuries, foregoing the activity which caused the tendinitis or epicondylitis in the elbow is usually the most effective treatment. Patients, however, are often unwilling to forego the offending activity for an extended period of time. Thus, numerous devices have been developed in an attempt to reduce the stress on the elbow joint which occurs during exercise. For example, U.S. Pat. No. 3,789,842 describes a therapeutic support device comprising a flexible, but non-elastic band which is secured about the forearm adjacent to the elbow. The band is tightly secured about the forearm, and, because of its non-elastic nature, resists the expansion of the forearm muscles. A similar device is shown in U.S. Pat. No. 3,877,426.

While these prior art devices will often lessen discomfort when used during the offending activity (i.e., tennis), none are designed to reduce stress in the tendon/epicondyle area during the recuperative period which leads to healing. In addition, many of these devices are rather bulky and apply a considerable amount of compression about the forearm, and are thus not suitable for continual use. Thus, there is a need for a therapeutic device which will continually reduce the stress on the tendon/epicondyle area of the elbow, and which may be worn for long periods of time without discomfort.

SUMMARY OF THE INVENTION

It is an object of the present invention to provide a therapeutic device for treating tendinitis and epicondylitis of the elbow.

It is another object of the present invention to provide a therapeutic device for treating tendinitis and epicondylitis of the elbow, wherein the device may be continually worn during recuperative periods.

It is yet another option of the present invention to provide a method for treating tendinitis or epicondylitis of the elbow using the therapeutic device of the present invention.

The foregoing objects may be accomplished by providing a therapeutic device for treating tendinitis and epicondylitis of the elbow, wherein this device comprises a loop of elastic material, said loop having a 360-degree twist built therein so as to provide distinct first and second surfaces on said loop. The loop may comprise a strip of elastic material, said strip having first and second ends, wherein said first end of the strip is rotated 360-degrees and alignably attached to said second end. The strip preferably has a width less than about 3 inches, and the elastic material is preferably a stretchable fabric. The first and second ends of the strips may be attached by means of stitching, and diametrically opposed portions of the first and second surfaces of the loop may be secured to one another to thereby provide a figure-8 configuration for said loop. The fastening of the diametrically opposed portions of the first and second surfaces of said loop may be accomplished using a releasable fastener (e.g., a button or hook and loop fastener), or by stitching.

A method for treating tendinitis or epicondylitis of the elbow joint of a patient is also provided, and this method comprises the steps of:

(a) providing a therapeutic device comprising a loop of elastic material;

(b) positioning said loop about the elbow joint in a figure-8 formation, such that said loop is divided into an upper-band and a lower-band wherein said bands intersect at a crossover point, wherein said upper-band encircles the arm above and adjacent said elbow joint, said lower-band encircles the arm below and adjacent said elbow joint, and said crossover point is positioned in the crease of said elbow joint; and (c) permitting said loop to remain positioned about said elbow joint for a period sufficient to provide the desired relief.

Both the elastic material and the circumferential length of the loop may be selected so as to ensure that said upper- and lower-bands will apply sufficient pressure about the circumference of the arm to ensure that said device will remain in place, while still permitting said therapeutic device to be worn for an extended period of time without discomfort.

BRIEF DESCRIPTION OF THE DRAWINGS

While the specification concludes with claims particularly pointing out and distinctly claiming the present invention, it is believed that the same will be better understood from the following description taken in conjunction with the accompanying drawings in which:

DETAILED DESCRIPTION OF THE INVENTION

Reference will now be made in detail to the presently preferred embodiments of the invention, examples of which are illustrated in the accompanying drawings, wherein like numerals indicate the same elements throughout the views.

Figure 2:
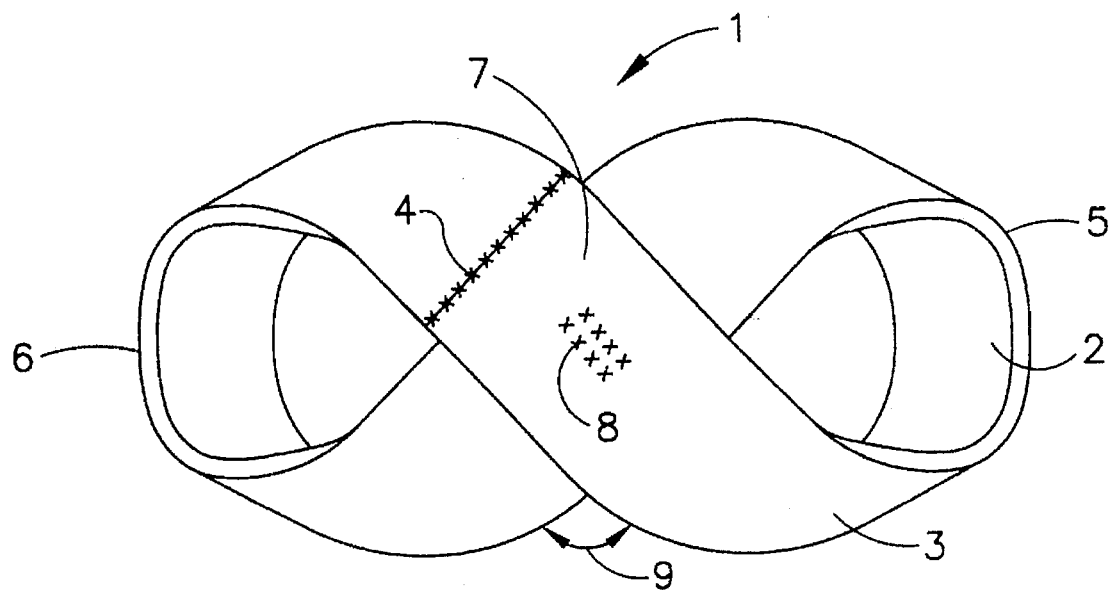
FIG. 2 is a perspective view of another embodiment of the therapeutic device of the present invention.

FIG. 2 depicts one embodiment of a therapeutic device according to the present invention. The device 1 comprises a loop of elastic material, wherein the loop has a 360-degree twist built therein in order to provide distinct first surface 2 and second surface 3. In other words, one may continuously traverse either first surface 2 or second surface 3 without ever leaving that surface.

The device may be readily prepared from an untwisted loop of elastic material (such as an absorbent head band) by first cutting the untwisted loop transversely across its width, thereby resulting in a strip of elastic material having a length corresponding to the previous circumference of the untwisted loop. One end of this strip of material is then rotated 360 degrees, and then reattached to the opposite end of the strip, thereby forming a loop having a 360-degree twist built therein. As shown in FIG. 2, after rotation the ends of the strip may be reattached by stitching 4 or other suitable means. Of course, as an alternative, device 1 may be formed directly during the manufacturing process, such as by weaving the material into the final twisted configuration. The device of FIG. 2 is similar to a Mobius strip, however therapeutic device 1 has a 360-degree twist built therein rather than the 180-degree twist of a Mobius strip.

As also shown in FIG. 2, device 1 will naturally form the figure-eight formation shown. This figure-eight formation divides the loop into an upper-band 5 and a lower-band 6, wherein the upper and lower bands intersect at crossover point 7. As will be apparent to one skilled in the art, device 1 can therefore also be manufactured by attaching two loops of material to one another in the manner shown.

Figure 3:
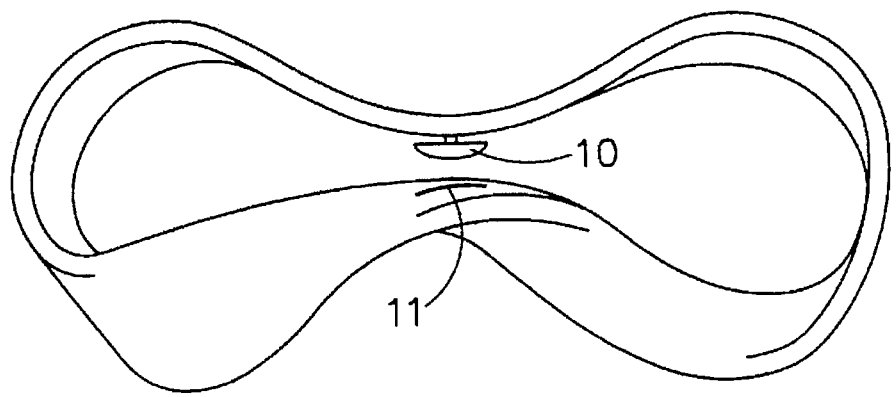
FIG. 3 is yet another embodiment of the therapeutic device of the present invention.

While device 1 will naturally form the figure-eight formation shown in FIG. 2, as will be understood in more detail after the use of the device is described, it may often be desirable to secure device 1 in the figure-eight formation by means of stitching 8. Thus, diametrically opposed portions of first surface 2 and second surface 3 are stitched to one another in the manner shown in FIG. 2 in order to secure the figure-eight/formation from the twisted loop of elastic material. Prior to stitching, the loop is preferably positioned such that angle 9 is between about 70 degrees and about 110 degrees, more preferably about 90 degrees. As an alternative to stitching 8 shown in FIG. 2, other suitable fastening means may be employed. For example, as shown in FIG. 3, a simple button 10 and corresponding button-hole 11 are provided. Another alternative is the use of a hook and loop fastener system (e.g., Velcro). One advantage of not securing device 1 in the figure-eight formation, however, is that the user may continually adjust the placement of device 1 on their arm to a greater degree thereby ensuring more comfort.

Figure 1:
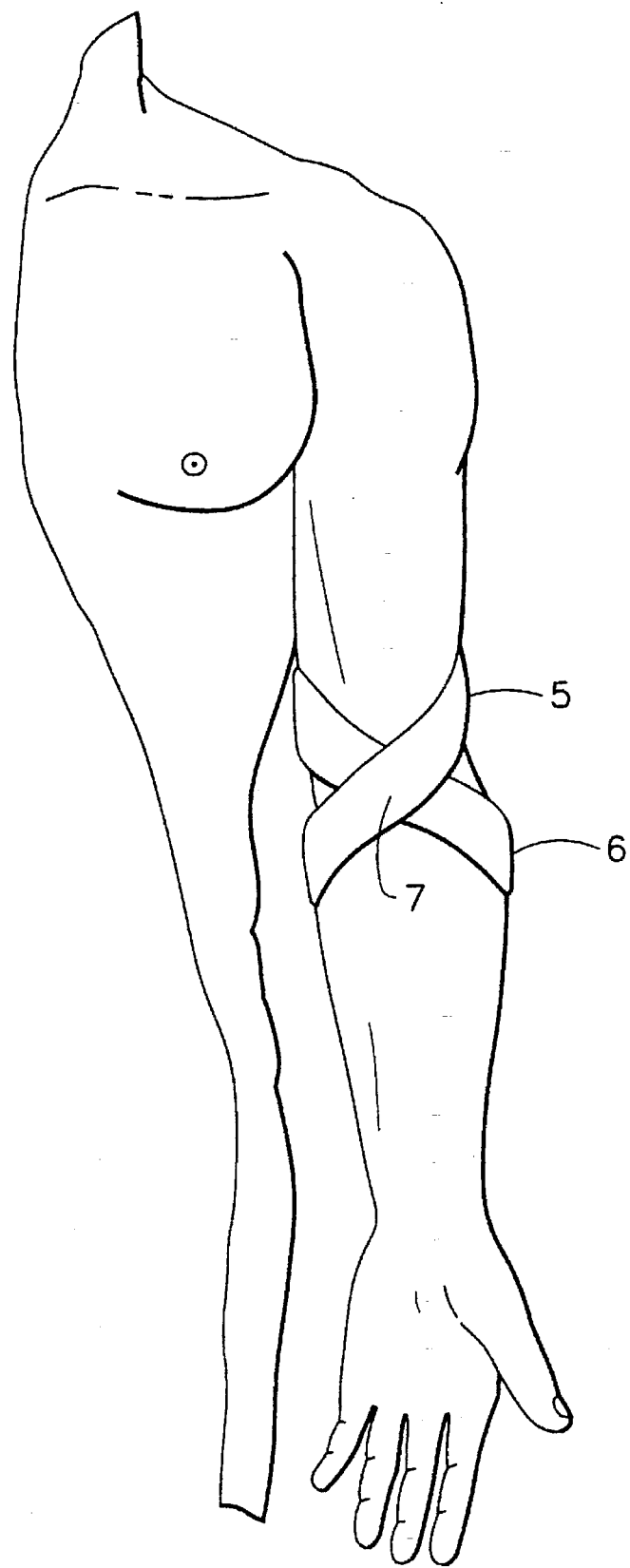
FIG. 1 is a front view of one embodiment of the therapeutic device of the present invention, wherein the device has been properly placed upon the patient's arm.

FIG. 1 depicts the proper use of therapeutic device 1. It should first be noted, that device 1 shown in FIG. 1 was not preformed into the figure-eight formation, such as by the stitching 8 or button 10 described above. Thus, therapeutic device 1 is positioned in the figure-eight formation by the user, and the user inserts their arm into upper-band 5 and lower-band 6. Device 1 is then slid upward on the arm until upper-band 5 encircles the arm above and adjacent the elbow joint, and lower-band 6 encircles the arm below and adjacent to the elbow joint. Crossover point 7 is then positioned in the crease of the elbow joint as shown in FIG. 1. When positioned properly, only first surface 1 will contact the arm of the user, as the 360-degree twist built into the device ensures a continual, smooth contact between first surface 1 and the arm of the user. In fact, the only portion of first surface 1 which does not directly contact the user's arm is the small portion positioned at crossover point 7. Thus, the therapeutic device of the present invention may be worn by the user with great comfort since there are no creases or twists which contact the user.

It is generally preferred that the dimensions of upper-band 5 and lower-band 6 are approximately equal, and the dimensions of the loop of elastic material (as well as the elastic material itself) may readily be chosen to provide the desired pressure on the user's arm. As will be more fully discussed below, the therapeutic device of the present invention need only provide light continuous pressure about the user's arm. Essentially, the pressure should be only slightly greater than that required to hold the device in place. Since arm sizes vary, the dimensions of the device can also be modified for a proper fit. Preferably, several sizes of the device are provided in order to ensure and provide a proper fit for any potential user.

The elastic material used to manufacture therapeutic device 1 can vary widely greatly. A presently preferred material for the therapeutic device of the present invention is cotton terry of the type commonly used in the manufacture of sweatbands. The cotton terry material provides a light pressure about the circumference of the arm, and is extremely comfortable for the user. In addition, this material can be readily washed and quickly dried for immediate reuse. The device of the present invention can even be manufactured directly from such a sweatband by the method described previously. Numerous other elastic materials can also be employed, however, including: cotton velour, lambs wool and spandex. Thus, the present invention is not limited to cotton terry.

When used in the manner shown in FIG. 1, the therapeutic device of the present invention has proven to be surprisingly effective in treating tendinitis and epicondylitis. It is believed that the gentle pressure imparted by lower-band 6 about the circumference of the forearm acts to dampen the repeated vibrations of the tendons associated with the elbow joint, thereby relieving stresses placed on the tendon-epicondyle junctions. In other words, lower-band 6 will cause the tendons to react similarly to a vibrating string of a musical instrument string which is pressed slightly (i.e., vibration eliminated). This in turn will reduce the amount of pulling on the epicondyle-tendon junction, thereby reducing the strain placed upon this juncture. Since even the smallest movement of the arm causes some vibration in the tendons, device 1 will greatly reduce the stress on the tendons and epicondyles during periods of non-exercise, thereby promoting the healing process (i.e., reduction of inflammation). Device 1, therefore, provides an effective treatment for epicondylitis and tendinitis of the elbow during the recuperative period which leads to healing, particularly when combined with other treatments such as ice and anti-inflammatory medications, and will permit the user to return to the offending activity much sooner than would otherwise be possible.

While it is believed that the gentle pressure placed on the tendons of the forearm are primarily responsible for hastening the healing process, it is also believed that the gentle pressure on the lower bicep and tricep tendons of the upper arm imparted by upper-band 5 further assists in the healing by reducing the stresses placed upon these tendons in the same manner as described previously. The primary purpose of upper-band 5, however, is to stabilize device 1 and hold it in proper position. This permits device 1 to be manufactured so that a gentle pressure is applied about the forearm, while still ensuring that therapeutic device 1 remains in place. Without upper-band 5, device 1 would have to be manufactured such that lower-band 6 would provide a much greater amount of force about the forearm in order that it would remain in place (such as the case in U.S. Pat. Nos. 3,789,842 and 3,877,426).

While single strap devices designed to tightly encircle the forearm may prove more effective for use during the activity causing the tendinitis or epicondylitis, these devices are generally not appropriate for round-the-clock use. In contrast, therapeutic device 1 of the present invention reduces the daily exacerbation of the tendinitis and epicondylitis, and facilitates the healing process by reducing the continuous stresses caused by normal daily activities outside of those which initially cause the problem.

While therapeutic device 1 of the present invention may be worn during the athletic endeavors which cause the injury, it will generally not prevent tendinitis or epicondylitis. It will, however, greatly assist in alleviating the problem once it has developed, particularly when combined with periods of recuperative resting of the elbow joint. In many cases, marked improvement will be observed within a few hours of use. Because of the gentle pressure applied about the arm, however, the user may continue to employ the device, even while sleeping, without discomfort. Continuing use will not only assist in returning the elbow joint to normalcy, but will also yield a stronger tendon/bone connection which is less likely to be reinjured during subsequent activity.

The foregoing description of the preferred embodiments is by no means exhaustive of the variations of the present invention that are possible, and has therefore been presented only for purposes of illustration and description. Obvious modifications and variations will be apparent to those skilled in the art in light of the teachings of the foregoing description. For example, an equivalent device could be manufactured by merely connecting an upper-band and a lower-band to form the resulting figure-eight configuration without the need to start from a continuous loop. Thus, it is intended that the scope of the present invention be defined by the claims appended hereto.

What I claim is:

1. A method for treating tendinitis or epicondylitis of the elbow joint of a patient, comprising the steps of:

(a) providing a therapeutic device consisting essentially of a loop of elastic material;

(b) positioning said loop about the elbow joint in a figure-8 formation, such that said loop is divided into an upper-band and a lower-band wherein said bands intersect at a crossover point, wherein said upper-band encircles the arm above and adjacent said elbow joint, said lower-band encircles the arm below and adjacent said elbow joint, and said crossover point is positioned in the crease of said elbow joint; and (c) permitting said loop to remain positioned about said elbow joint for a period sufficient to provide the desired relief.

2. The method of claim 1, wherein both the elastic material and the circumferential length of said loop are selected so as to ensure that said upper- and lower-bands will apply sufficient pressure about the circumference of the arm to ensure that said device will remain in place, while still permitting said therapeutic device to be worn for an extended period of time without discomfort.

3. The method of claim 2, wherein said elastic material is a stretchable fabric.

4. The method of claim 1, wherein said loop has a 360-degree twist built therein so as to provide distinct first and second surfaces on said loop, and wherein only said first surface will contact the patient's arm when said loop is positioned about the patient's elbow joint.

5. The method of claim 4, wherein said loop is provided in a preformed figure-8 formation in order to facilitate proper positioning of said device.

6. The method of claim 1, wherein both the elastic material and the circumferential length of said loop are selected so as to ensure that said upper- and lower-bands apply a gentle pressure about the circumference of the arm which is slightly greater than that required to ensure that the therapeutic device remains positioned about the elbow joint.

7. The method of claim 3, wherein said elastic material is cotton terry.

8. The method of claim 4, wherein said loop comprises a strip of elastic material, said strip having first and second ends, wherein said first end is rotated 360-degrees and alignably attached to said second end to thereby provide said 360-degree twist.

9. The method of claim 8, wherein said first and second ends are attached by means of stitching.

10. The method of claim 4, wherein diametrically opposed portions of said first and second surfaces of said loop are secured to one another to thereby provide said figure-8 formation.

11. The method of claim 10, wherein diametrically opposed portions of said first and second surfaces are secured to one another by stitching.

12. The method of claim 10, wherein diametrically opposed portions of said first and second surfaces are secured to one another by a releasable fastener.

13. The method of claim 6, wherein said elastic material is a stretchable fabric.

14. The method of claim 13, wherein said material is cotton terry.

\* \* \* \* \*